(12) United States Patent
Fujisaki et al.

(10) Patent No.: US 9,381,248 B2
(45) Date of Patent: Jul. 5, 2016

(54) COATING AGENT FOR PHARMACEUTICAL SOLID PREPARATION, PHARMACEUTICAL FILM FORMULATION, AND COATED PHARMACEUTICAL SOLID PREPARATION

(75) Inventors: Yuki Fujisaki, Kamakura (JP); Ryoji Yoshii, Mishima (JP); Suguru Takaki, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/819,523

(22) PCT Filed: Aug. 31, 2011

(86) PCT No.: PCT/JP2011/069692
§ 371 (c)(1),
(2), (4) Date: Feb. 27, 2013

(87) PCT Pub. No.: WO2012/029820
PCT Pub. Date: Mar. 8, 2012

(65) Prior Publication Data
US 2013/0156829 A1    Jun. 20, 2013

(30) Foreign Application Priority Data
Aug. 31, 2010    (JP) ................. 2010-194355

(51) Int. Cl.
*A61K 47/10* (2006.01)
*A61K 9/28* (2006.01)
*A61K 47/02* (2006.01)

(52) U.S. Cl.
CPC ............... *A61K 47/10* (2013.01); *A61K 9/2813* (2013.01); *A61K 9/2853* (2013.01); *A61K 47/02* (2013.01)

(58) Field of Classification Search
CPC .... A61K 9/2813; A61K 47/02; A61K 9/7007
See application file for complete search history.

(56) References Cited

U.S. PATENT DOCUMENTS

| | | | | |
|---|---|---|---|---|
| 2,766,209 | A * | 10/1956 | Marshall et al. | 508/136 |
| 3,383,237 | A * | 5/1968 | Tuerck | A61K 9/282 424/482 |
| 4,476,271 | A * | 10/1984 | Kano et al. | 524/377 |
| 5,556,639 | A | 9/1996 | Fielden | |
| 5,639,561 | A * | 6/1997 | Uhlemayr | 428/537.5 |
| 2003/0064036 | A1 | 4/2003 | Petereit et al. | |
| 2006/0229383 | A1 | 10/2006 | Noami et al. | |
| 2009/0274732 | A1 | 11/2009 | Hoffmann et al. | |
| 2009/0291123 | A1 | 11/2009 | Hoffmann et al. | |
| 2010/0233262 | A1 | 9/2010 | Kato et al. | |
| 2011/0256189 | A1 | 10/2011 | Hayashi et al. | |

FOREIGN PATENT DOCUMENTS

| | | | |
|---|---|---|---|
| CA | 2251886 A1 | 4/1997 | |
| CA | 2744008 A1 * | 7/2010 | ........... A61K 9/2813 |
| IL | WO 2004037226 A2 * | 5/2004 | ........... A61K 9/2866 |
| JP | 2000-508673 A | 7/2000 | |
| JP | 2000-273045 A | 10/2000 | |
| JP | 2003-509339 A | 3/2003 | |
| JP | 2004-518750 A | 6/2004 | |
| JP | 2006-188490 A | 7/2006 | |
| JP | 2009-521518 A | 6/2009 | |
| JP | 2009-539896 A | 11/2009 | |
| JP | 2009-539897 A | 11/2009 | |
| JP | 2010-513329 A | 4/2010 | |
| KR | 2009-0128918 | 12/2009 | |
| WO | 01/04195 A1 | 1/2001 | |
| WO | WO 2004037226 A2 * | 5/2004 | |
| WO | 2005/019286 A1 | 3/2005 | |
| WO | 2006/123765 A1 | 11/2006 | |
| WO | 2007/074110 A1 | 7/2007 | |
| WO | 2007/145191 A1 | 12/2007 | |
| WO | 2008/041663 A1 | 4/2008 | |
| WO | 2008/074145 A1 | 6/2008 | |
| WO | 2008/088776 | 7/2008 | |
| WO | 2009/099734 | 8/2009 | |
| WO | 2010/074223 A1 | 7/2010 | |
| WO | 2012/025730 | 3/2012 | |

OTHER PUBLICATIONS

Porter, S.C. "Coating of Pharmaceutical Dosage Forms" Remington: The Science and Practice of Pharmacy. 21st Edition. 2005. Chapter 46, pp. 929-938.*
Asada, M.; Nakashima, H.; Ishii, T.; Horiuchi, S. "Field Test of Ethanol/Bentonite Slurry Grouting into Rock Fracture" Mat. Res. Soc. Symp. Proc. 2006, 932, 1-8.*

* cited by examiner

*Primary Examiner* — Timothy Thomas
*Assistant Examiner* — Andrew S Rosenthal
(74) *Attorney, Agent, or Firm* — DLA Piper LLP (US)

(57) ABSTRACT

A coating agent for a pharmaceutical solid preparation imparts an unpackaged pharmaceutical solid preparation with excellent barrier properties equivalent to those of a PTP sheet without affecting the disintegration properties of the pharmaceutical solid preparation. The coating agent for a pharmaceutical solid preparation includes a polyethylene glycol having an average molecular weight of 950 to 25,000 and a swelling clay, wherein the mass ratio of the polyethylene glycol and the swelling clay is 2:8 to 6:4.

18 Claims, 4 Drawing Sheets

COATING AGENT FOR PHARMACEUTICAL SOLID PREPARATION, PHARMACEUTICAL FILM FORMULATION, AND COATED PHARMACEUTICAL SOLID PREPARATION

RELATED APPLICATIONS

This application is a §371 of International Application No. PCT/JP2011/069692, with an international filing date of Aug. 31, 2011 (WO 2012/029820 A1, published Mar. 8, 2012), which is based on Japanese Patent Application No. 2010-194355, filed Aug. 31, 2010, the subject matter of which is incorporated herein by reference.

TECHNICAL FIELD

This disclosure relates to a coating agent for a pharmaceutical solid preparation, a pharmaceutical film formulation and a coated pharmaceutical solid preparation.

BACKGROUND

A number of pharmaceuticals are not stable against oxygen and water vapor. Therefore, most of the commercially available pharmaceuticals, especially pharmaceutical solid preparations, are packaged with a packaging material such as a PTP (press through pack) sheet and protected from oxygen and water vapor.

Meanwhile, at medical sites and dispensing pharmacies, to prevent patients from forgetting to take their prescribed drugs and making mistakes in the dosage thereof, it is widely practiced to use single-dose package prepared by taking out a plurality of pharmaceuticals to be taken at once from the respective packages of PTP sheet or the like and provide the pharmaceuticals altogether in one bag. Furthermore, in western countries, patients often remove their pharmaceuticals from the respective packages of PTP sheet or the like and place them in separate pill cases or the like for storage. Therefore, there has been a demand for a method of improving the water vapor barrier property and oxygen barrier property, that is, gas barrier properties, of a pharmaceutical solid preparation itself.

As a method of improving the gas barrier properties of a pharmaceutical solid preparation itself, methods of sugar-coating a pharmaceutical solid preparation and methods of film-coating with a polymeric substance have been put into practice. For instance, there have been developed a film coating agent in which stearic acid is blended with aminoalkyl methacrylate copolymer E (Eudragit EPO (registered trademark); Degussa Co.) (Japanese Translated PCT Patent Application Laid-open No. 2004-518750); a resin composition obtained by copolymerizing a polyvinyl alcohol with a polymerizable vinyl monomer (WO 2005/019286); a coating agent obtained by adding talc and a surfactant to a polyvinyl alcohol (JP 2006-188490 A); and a film coating agent in which bentonite is uniformly dispersed in the form of a certain structure in PVA (WO 2010/074223).

Furthermore, the needs for a gas barrier film coating against those substances other than oxygen and water vapor include the needs of preventing volatile (subliminal) drugs or their decomposition products from being spread. When such substances are spread, they may generate a bad odor and/or cause problems of, for example, color change of other drugs when combined in a single-dose formulation. For example, in olmesartan medoxomil preparations which are angiotensin II receptor antagonists, it is known that the (5-methyl-2-oxo-1,3-dioxol-4-yl)methyl group released from olmesartan medoxomil is hydrolyzed into diacetyl to cause a diacetyl-originated odor. Further, olmesartan medoxomil preparations are also known to induce color change in a metformin hydrochloride preparation when placed in a single-dose package with a metformin hydrochloride preparation and stored under a high-temperature and high-humidity condition. This color change is caused by a reaction between diacetyl originated from olmesartan medoxomil and the guanidino group of metformin hydrochloride.

As a method improving such odor and color change problems, there have been reported a pharmaceutical package comprising a chemisorptive drying agent (WO 2008/041663), a film coating comprising carboxymethylcellulose (WO 2006/123765) and a coating comprising a polyvinyl alcohol copolymer (WO 2007/145191).

However, not only does it require a long time to sugar-coat a pharmaceutical solid preparation for the purpose of attaining gas barrier properties, but such sugar coating also has a large thickness and it thus enlarges the pharmaceutical solid preparation itself, so that it may impose a burden upon patients for taking such a large pharmaceutical solid preparation and may also extend the time required for the drug to take effect.

Moreover, among those conventional methods of film-coating a pharmaceutical solid preparation with a polymeric substance, only the film coating agent of WO '223 can attain excellent gas barrier properties equivalent to a PTP sheet (water vapor permeability: less than $1.0 \times 10^{-4}$ g·mm/cm$^2$·24 hr·atm, oxygen permeability coefficient: less than $1.0 \times 10^{-4}$ cm$^3$·mm/cm$^2$·24 hr·atm) and those gas barrier properties that are obtained by other methods are not comparable to those of a PTP sheet.

Furthermore, with regard to the film coating agent of WO '223, since the disintegrating force of the resulting film itself is weak, it has been pointed out not only that a delay in disintegration may occur to affect the drug effect when the disintegration properties of a pharmaceutical solid preparation to be coated are not sufficient, but also that the bioequivalence test associated with formulation change may become more troublesome.

Therefore, it could be helpful to provide a coating agent for a pharmaceutical solid preparation which imparts an unpackaged pharmaceutical solid preparation with excellent barrier properties equivalent to those of a PTP sheet without affecting the disintegration properties of the pharmaceutical solid preparation.

SUMMARY

We discovered that a coating agent in which a swelling clay is uniformly dispersed in a polyethylene glycol is capable of imparting a pharmaceutical solid preparation with gas barrier properties equivalent to those of a PTP sheet and that a film formed by the coating agent has excellent disintegration properties.

We thus provide a coating agent for a pharmaceutical solid preparation which comprises a polyethylene glycol having an average molecular weight of 950 to 25,000 and a swelling clay, wherein the mass percent of the polyethylene glycol and the swelling clay is 20:80 to 60:40.

By using the above-described film coating agent to form a thin film on the surface of a pharmaceutical solid preparation to coat the pharmaceutical solid preparation with the film layer, due to the effect of the mass percent of the polyethylene glycol and the swelling clay and the effect of the swelling clay being in a swollen state, the swelling clay forms a labyrinth-like structure and exhibits an effect of preventing the thus coated pharmaceutical solid preparation from coming into contact with water vapor and oxygen (hereinafter, referred to as "labyrinth effect"). By this, even when the film layer is thin, the pharmaceutical solid preparation itself can be imparted with excellent gas barrier properties that are equivalent to those of a PTP sheet so that the pharmaceutical solid preparation can be taken by patients without any problem.

It is preferred that the above-described swelling clay be bentonite or magnesium aluminum silicate.

By using bentonite or magnesium aluminum silicate, superior labyrinth effect can be attained.

It is preferred that the above-described coating agent contain a sugar alcohol derivative-type surfactant in an amount of 0.5 to 30%.

It is preferred that the above-described sugar alcohol derivative-type surfactant be a sorbitan fatty acid ester.

Also, we provide a pharmaceutical film formulation composed of the above-described coating agent and having a water vapor permeability of less than $1.0 \times 10^{-4}$ g·mm/cm$^2$·24 hr·atm at a room temperature of 40° C. and a relative humidity of 75%; and a coated pharmaceutical solid preparation coated with the above-described coating agent and having a water vapor permeability of less than $1.0 \times 10^{-4}$ g·mm/cm$^2$·24 hr·atm at a room temperature of 40° C. and a relative humidity of 75%.

Further, we provide a pharmaceutical film formulation which comprises a polyethylene glycol having an average molecular weight of 950 to 25,000 and a swelling clay, wherein the mass percent of the above-described polyethylene glycol and the above-described swelling clay is 20:80 to 60:40 and the water vapor permeability at a room temperature of 40° C. and a relative humidity of 75% is less than $1.0 \times 10^{-4}$ g·mm/cm$^2$·24 h·atm; and a coated pharmaceutical solid preparation which has a coating layer comprising a polyethylene glycol having an average molecular weight of 950 to 25,000 and a swelling clay, in which coating layer the mass percent of the above-described polyethylene glycol and the above-described swelling clay is 20:80 to 60:40 and the water vapor permeability at a room temperature of 40° C. and a relative humidity of 75% is less than $1.0 \times 10^{-4}$ g·mm/cm$^2$·24 h·atm.

Since excellent gas barrier properties equivalent to those of a PTP sheet can be imparted to a pharmaceutical solid preparation itself even when it is in an unpackaged condition, deterioration of the pharmaceutical solid preparation can be prevented and its medicinal component(s) can be stably retained for a prolonged period of time. Further, since the formed film itself has excellent disintegration properties, it can exhibit excellent gas barrier performance without affecting the disintegration properties of the pharmaceutical solid preparation.

BRIEF DESCRIPTION OF THE DRAWINGS

FIG. 2-1 shows the dissolution profiles of the tablets of Example 2 and Comparative Example 5 and a commercially available tablet.

FIG. 2-2 shows the dissolution profiles of the tablet of Example 2 before and after storage.

FIG. 2-3 shows the dissolution profiles of the tablet of Comparative Example 5 before and after storage.

FIG. 2-4 shows the dissolution profiles of a commercially available tablet before and after storage.

DETAILED DESCRIPTION

Examples will now be described. However, this disclosure is not restricted to the examples and descriptions below. It is noted here that, unless otherwise specified, "%" represents "% by mass (w/w %)."

The coating agent for a pharmaceutical solid preparation is characterized in that it comprises a polyethylene glycol having an average molecular weight of 950 to 25,000 and a swelling clay and that the mass percent of the polyethylene glycol and the swelling clay is 20:80 to 60:40.

The term "pharmaceutical solid preparation" used herein refers to a pharmaceutical formulated in the form of a solid and examples thereof include tablets (such as sublingual tablets and orally-disintegrating tablets), capsules (such as soft capsules and microcapsules), granules, subtle granules, powders, pills, troches and film formulations.

The term "coating agent for a pharmaceutical solid preparation" used herein refers to a composition which is capable of forming a thin film on the surface of a pharmaceutical solid preparation to coat the pharmaceutical solid preparation with a layer of the film. The above-described film imparts gas barrier properties to a pharmaceutical solid preparation and plays a role in inhibiting, for example, degradation of a medicinal component contained in the pharmaceutical solid preparation by oxygen or water vapor, as well as color change or deterioration of the pharmaceutical solid preparation.

It is preferred that the mass of the film layer coating a pharmaceutical solid preparation be 2 to 200% with respect to the mass of the pharmaceutical solid preparation itself and, in cases where the pharmaceutical solid preparation is a tablet, the mass of the film layer is preferably 3 to 70%, more preferably 3 to 20%, still more preferably 3 to 15%.

To form a thin film layer on the surface of a pharmaceutical solid preparation using the coating agent for a pharmaceutical solid preparation, the coating agent for a pharmaceutical solid preparation may be, for example, sprayed or coated onto the surface of the pharmaceutical solid preparation and the solvent contained in the coating agent may then be removed by drying. More specifically, in cases where the pharmaceutical solid preparation is in the form of a tablet, for example, a coating pan or a tablet coating machine may be employed. Further, in cases where the pharmaceutical solid preparation is in the form of granules or powder, for example, a fluidized bed coating machine or a tumbling fluidized bed coating machine may be employed.

Examples of the solvent contained in the above-described coating agent include water, $C_1$ to $C_5$ lower alcohols and mixed solvents thereof, and the above-described solvent is preferably ethanol or water.

Further, the coating agent for a pharmaceutical solid preparation may not only be in a liquid state, but also in a solid state. Examples of the coating agent in a solid state include those obtained by spray-drying or freeze-drying a liquid coating agent and evaporating its solvent component.

A film formulation can be obtained also by adding a medicinal component to the coating agent for a pharmaceutical solid preparation and then drying the resultant as is.

The "medicinal component" contained in the pharmaceutical solid preparation refers to one which is used in the treatment, prevention and/or diagnosis of a human or animal disease and is not an equipment or an apparatus. Examples of such medicinal component include chemotherapeutic agents, calcium antagonists, antibiotics, respiratory stimulants, antitussive-expectorants, antineoplastic agents, autonomic agents, psychotropic agents, local anesthetics, muscle relaxants, drugs for digestive organs, antihistamines, toxicopetic agents, hypnosedatives, antiepileptics, antipyretic agents, analgesic agents, anti-inflammatory agents, cardiac stimulants, antiarrhythmic agents, diuretic agents, vasodilators, antilipemic agents, analeptic modifying agents, vitamin preparations, anticoagulants, hepatic drugs, hypoglycemic agents, hypotensive agents, colitis therapeutic agents, antiasthmatic agents, antianginal agents, antiemetic agents, glucocorticoids, therapeutic agents for ulcerative colitis and Crohn's disease, antifungal agents, arteriolosclerosis therapeutic agents, enzyme inhibitors, gout therapeutic agents, anti-Parkinson drugs, migraine therapeutic agents, proteins and peptides. The excellent gas barrier properties that are attained by the coating agent for a pharmaceutical solid preparation sufficiently exhibit the effects thereof particularly in coating of a pharmaceutical solid preparation containing a medicinal component having a moisture-absorbing property, oxidative degradation property or odor property.

The term "deterioration of a pharmaceutical solid preparation" used herein refers to, for example, a change in the weight, hardness or shape of a pharmaceutical solid preparation caused by oxygen or water vapor; a reduction or leakage of the medicinal component content due to decomposition; cracking on the surface of a pharmaceutical solid preparation; or a change in the outer appearance such as coloration.

The term "polyethylene glycol" (hereinafter, referred to as "PEG") used herein refers to a polymeric compound (polyether) having a structure of polymerized ethylene glycol and such a polymeric compound is referred to as "Macrogol" in the Japanese and European Pharmacopoeias and "polyethylene glycol" in the U.S. Pharmacopoeia (NF). Since the product number of each grade and its average molecular weight are not uniformly defined among these three pharmacopeias, the product name of a PEG is hereinafter indicated with the designation used by the Japanese Pharmacopoeia. The PEG is required to have an average molecular weight of 950 to 25,000 (for example, Japanese Pharmacopoeia Macrogol 1000, 4000, 6000 or 20000 (manufactured by NOF Corporation or Sanyo Chemical Industries, Ltd.)) and in particular, the PEG is preferably one having an average molecular weight of 7,000 to 9,300 (for example, Japanese Pharmacopoeia Macrogol 6000). As long as the average molecular weight is in the above-described range, a plurality of PEGs having different average molecular weights may be used in combination as well.

The term "swelling clay" used herein refers to a clay having a swelling property. More specifically, the term refers to, among those fine powder substances that exhibit viscosity and plasticity when containing an appropriate amount of water, a substance having a swelling property.

As the swelling clay, one which is negatively charged due to the composition balance of the metal salt species is preferred, and examples of such negatively charged swelling clay include smectites having a three-layer structure.

The term "negatively charged" refers to a condition in which the swelling clay has a cation exchange capability and the amount of the change is expressed in terms of the cation exchange capacity (CEC). The unit of the cation exchange capacity is milliequivalent/100 g (hereinafter, indicated as "meq/100 g") and generally expressed in terms of the number of equivalents corresponding to the molar concentration of monovalent ions.

Examples of the smectites include beidellite, nontronite, saponite, hectorite, sauconite, bentonite (hereinafter, referred to as "BT"), aluminum magnesium silicate and mixtures thereof. Thereamong, BT and aluminum magnesium silicate are preferred and BT is more preferred.

It is preferred that the swelling clay be uniformly dispersed in a film formed by the above-described coating agent for a pharmaceutical solid preparation. As an "uniformly dispersed" condition, one in which the swelling clay is dispersed as a single-layer belt-like structure is most preferred. However, it is difficult to exfoliate the swelling clay down to single layer with a production equipment normally used in the production of a pharmaceutical product. Practically, the swelling clay is preferably in a condition where it is dispersed in the form of a belt-like laminated structure having 10 to 100 layers of belt-like structures, and it is preferred that the number of layers in the belt-like laminated structure be as small as possible. This is because, in a film formed by the coating agent which contains BT and a polymer in certain amounts, by allowing the swelling clay to be uniformly dispersed in the form of a belt-like laminated structure having a small number of layers, a superior labyrinth effect can be attained and the gas barrier performance is consequently improved.

In the cross-section of a film formed by the coating agent for a pharmaceutical solid preparation in the thickness direction, it is preferred that the above-described belt-like laminated structure be dispersed in a mesh pattern and planarly oriented. The condition of the belt-like laminated structure at the cross-section in the film thickness direction can be observed under, for example, a transmission electron microscope (hereinafter, referred to as "TEM").

The term "mesh pattern" refers to a state in which the belt-like structure of the swelling clay is literally forming a mesh when the dispersion state of the belt-like laminated structure at the cross-section in the film thickness direction is expressed two-dimensionally.

The term "planarly oriented" refers to a state in which the belt-like structure of the swelling clay is laminated in the film thickness direction.

To allow the swelling clay to be dispersed as a belt-like laminated structure in a film formed by the coating agent for a pharmaceutical solid preparation, it is preferred that the swelling clay contained in the coating agent be in a swollen state.

The "swollen state" of the swelling clay refers to a state in which the swelling clay contains a dispersion medium and is swollen. Examples of swelling clay in a swollen state include a dispersion obtained by suspending a swelling clay in a dispersion medium and stirring the resulting suspension using a homogenizer or the like, and it is preferred that the swelling clay be dispersed in such a manner that all of the swelling clay can pass through a filter paper when the dispersion is filtered. Examples of the filter paper used in the above-described filtering operation include a glass fiber filter paper GF/D (particle retention capacity: 2.7 μm; manufactured by Whatman).

Examples of the index for the degree of dispersion of the swelling clay contained in the coating agent for a pharmaceutical solid preparation as a belt-like laminated structure include a haze value. A haze value represents the turbidity of the coating agent and it becomes smaller as the swelling clay is more uniformly dispersed and the coating agent becomes more transparent. That is, a smaller haze value of the coating agent indicates a smaller number of layers in the belt-like structure of the swelling clay. As the swelling clay contained in the coating agent for a pharmaceutical solid preparation, a 3.5% aqueous solution containing only the swelling clay whose haze value is not higher than 90% is preferred and one whose haze value is not higher than 60% is more preferred.

In the coating agent for a pharmaceutical solid preparation, the mass percent of the PEG and the swelling clay is required to be 20:80 to 60:40, and it is preferably 3:7.

In cases where the mass of the swelling clay is less than 40% of the mass of the PEG, the labyrinth effect provided by the swelling clay becomes small so that excellent gas barrier properties that are equivalent to those of a PTP sheet cannot be attained. Meanwhile, in cases where the mass of the swelling clay is greater than 4 times the mass of the PEG, since the mass percent of the swelling clay is excessively high, the dispersion of the swelling clay as a belt-like laminated structure becomes heterogeneous so that excellent gas barrier properties that are equivalent to those of a PTP sheet cannot be attained.

To sufficiently attain the labyrinth effect of the swelling clay, it is preferred that the mass percent of the swelling clay in a film formed by the above-described coating agent for a pharmaceutical solid preparation be not less than 20.

The water vapor permeability of a film formed by the coating agent for a pharmaceutical solid preparation is preferably $1.0 \times 10^{-5}$ to $1.0 \cdot 10^{-4}$ g·mm/cm²·24 hr·atm, which is equivalent to that of a PTP sheet, more preferably $1.0 \times 10^{-5}$ to $6.5 \times 10^{-5}$ g·mm/cm²·24 hr·atm, still more preferably $1.0 \times 10^{-5}$ to $3.0 \times 10^{-5}$ g·mm/cm²·24 hr·atm.

A film formed by the coating agent for a pharmaceutical solid preparation exhibits excellent disintegration properties. More specifically, in a dissolution test (37° C., paddle method, 50 rounds/min, solvent: 900 ml of water) of a film formed in a size of 1 cm×2 cm and a thickness of 60 μm, the film is disintegrated within 10 minutes to lose its shape.

It is important to uniformly disperse the swelling clay in the coating agent solution to allow the swelling clay to be uniformly dispersed in a film. As a dispersion apparatus therefor, an apparatus which has a stirring capability for uniformly dispersing the swelling clay as a belt-like laminated structure is preferred and, for example, a homogenizer (Polytron; Kinematica AG) or a thin-film spin system high-speed mixer (FILMIX; PRIMIX Corporation) is suitably employed.

The coating agent for a pharmaceutical solid preparation may also contain a pharmaceutically acceptable additive(s) within the range where the gas barrier properties of the coating agent are not impaired. For example, to make the dispersion of the swelling clay as a belt-like laminated structure more uniform, the coating agent may contain a surfactant as an additive. In this case, the amount of the surfactant with respect to the total amount of the PEG and the swelling clay is preferably 0.01 to 30 parts by mass percent, more preferably 1 to 20 parts by mass percent, still more preferably 5 to 15 parts by mass percent.

As the above-described surfactant, a sugar alcohol derivative-type surfactant is preferred. The term "sugar alcohol derivative-type surfactant" used herein refers to a compound which has a sugar alcohol skeleton in the molecule and exhibits surface-activating capability. Among such compounds, a sorbitan fatty acid ester is preferred, and examples thereof include sorbitan monolaurates.

In cases where a sugar alcohol derivative-type surfactant is used as an additive, it is preferred that the coating agent for a pharmaceutical solid preparation contain the sugar alcohol derivative-type surfactant in an amount of 0.5 to 30%.

The coating agent for a pharmaceutical solid preparation may further contain additives which are commonly used in coatings in the field of pharmaceuticals. Examples of such additive include colorants that are masking agents, such as plant-extracted dyes; titanium oxide; calcium carbonate; and silicon dioxide.

A pharmaceutical solid preparation to be coated with a film layer formed by the coating agent for a pharmaceutical solid preparation may also be coated in advance with a film layer formed by other polymeric substance or the like. In this case, it is preferred that the ratio of the swelling clay with respect to the amount of the whole film layer of the pharmaceutical solid preparation be not less than 5%.

EXAMPLES

Our coating agents, formulations and preparations will now be concretely described by way of examples thereof. However, this disclosure is not restricted thereto.

(Method of Measuring Water Vapor Permeability)

The water vapor permeability of a film formed by the coating agent for a pharmaceutical solid preparation was measured in accordance with JIS K8123 (1994) having minor modifications.

Specifically, a film which was formed by a coating agent prepared as appropriate was examined before the light and a portion of uniform thickness without pinhole was selected and cut into a round shape of 3.5 cm in diameter to measure the thickness of the film at 5 arbitrary spots. Then, 3 g of calcium chloride (850 to 2,000 μm in particle size) was placed in an aluminum cup (30 mm in diameter) and the film cut into a round shape and a film fixation ring were sequentially placed on the aluminum cup. A weight was placed on the ring to fix the ring, and in this condition, molten paraffin wax was poured into the margin of the aluminum cup. After the paraffin wax was solidified, the weight was removed and the mass of the aluminum cup as a whole was measured to determine the initial mass. Thereafter, the aluminum cup was placed in an incubator of 40° C. and 75% RH and the aluminum cup was taken out every 24 hours to measure the mass thereof. Then, using the following equation, the water vapor permeability coefficient was calculated. It is noted here that, in all of the below-described water vapor permeability measurement tests, r=1.5 cm, t=24 hours and C=1 atm.

Water Vapor Permeability (g·Mm/Cm²·24 hr·Atm)= $(W \times A)/(B \times t \times C)$ W: Increase in the mass in 24 hours (g)
A: Average film thickness at 5 spots (mm)
B: Permeation area, $\pi r^2$ (cm²)
t: Elapsed time (hour)
C: Atmospheric pressure (atm)

(Method of Measuring Haze Value)

Using an integrating sphere spectrophotometer (self-recording spectrophotometer, Model UV-3101PC; Shimadzu Corporation), the total light transmission spectrum and the diffusion-transmission spectrum were measured to calculate the haze value.

(Method of Measuring Oxygen Permeability Coefficient)

In accordance with JIS K7126-1 (2006) (Gas Permeability Test Method by Gas Chromatography), the oxygen permeability coefficient of a film formed by the coating agent for a pharmaceutical solid preparation was measured at a temperature of 23±2° C. and a relative humidity of 90% (90% RH) using an oxygen permeability coefficient measuring apparatus (GTR-30XAD2G and 2700T.F; GTR Tec Corporation).

(Dissolution Test of Sodium Valproate Preparation)

The dissolution test was performed in accordance with The Japanese Pharmacopoeia, 15th Edition: "Dissolution Test"

(2nd method). Using the Japanese Pharmacopoeia 2nd solution for dissolution fluid for dissolution test as a test solution, a tablet was loaded to 900 mL of the test solution and the eluted solution was collected with time and quantified under the following HPLC conditions.
<<HPLC Conditions>>
Mobile phase: 50 mM sodium dihydrogen phosphate/acetonitrile=5/5 (v/v)
Column: Devolosil ODS-5 (4.6×150 mm)
Detection wavelength: 210 nm
(Dissolution Test of Montelukast Sodium Preparation)

The dissolution test was performed in accordance with The Japanese Pharmacopoeia, 15th Edition: "Dissolution Test" (2nd method). A tablet was loaded to a test solution (900 mL) prepared by adding 0.5% polysorbate 80 to distilled water and the eluted solution was collected with time and quantified under the following HPLC conditions.
<<HPLC Conditions>>
Mobile phase: acetate buffer (pH 3.5)/methanol=15/85 (v/v)
Column: Hypersil ODS (4.6×250 mm)
Detection wavelength: 254 nm
(Calculation Method of Increase in Mass due to Moisture Absorption by Tablet (Increase in Moisture Absorption))

The mass of a tablet was measured before and after storage to calculate the increase in moisture absorption using Equation 1:

$$\text{Increase in moisture absorption (\% by mass)} = \{(W-Ws)/Ws\} \times 100 \quad \text{Equation 1}$$

W: Mass of tablet after storage (g)
Ws: Mass of tablet before storage (g).
(Method of Evaluating Tablet Coloration)

Using a spectrocolorimeter (JP7100F/C; JUKI Corporation), L*, a* and b* were measured, and the difference in the tablet color before and after storage (ΔE) was calculated using Equation 2:

$$\Delta E = \{(\Delta L)^2 + (\Delta a)^2 + (\Delta b)^2\}^{0.5} \quad \text{Equation 2}$$

ΔL: Difference in the brightness of tablet (L* axis) before and after storage
Δa: Difference in the value of red to green of tablet (a* axis) before and after storage
Δb: Difference in the value of yellow to blue of tablet (b* axis) before and after storage.

Example 1

To 445.1 parts by mass of water, 10.5 parts by mass of a PEG (Macrogol 6000 (average molecular weight: 7,300 to 9,300); NOF Corporation), 544.4 parts by mass of 4.5% BT solution and 3.5 parts by mass of Span20 were added, and the resultant was stirred using a homogenizer (Polytron (registered trademark) Model KR) to obtain a coating agent (hereinafter, referred to as "the coating agent of Example 1"). As the 4.5% BT solution, a filtrate which was obtained by adding 45 parts by mass of BT (Kunipia-F (cation exchange capacity: 115 meq/100 g); Kunimine Industries Co., Ltd.) to 955 parts by mass of stirred water, uniformly dispersing the resulting solution using a homogenizer, and then centrifuging the resultant and suction-filtering the thus obtained supernatant through a filter paper was employed.

To a coating pan (DRC-200; Powrex Corporation), 50 g of a sodium valproate tablet (Depakene (registered trademark) tablet, 200 mg; Kyowa Hakko Kirin Co., Ltd.) and 200 g of a placebo tablet (for bulking) were loaded, and the sodium valproate tablet was coated with the coating agent of Example 1 to a film thickness of 50 to 60 µm. The resulting coated sodium valproate tablet was stored for 12 days at a temperature of 40° C. and a relative humidity of 75% to examine the change in the outer appearance and the dissolution profile before and after the storage.

Further, the coating agent of Example 1 was sprayed onto the back side of a polypropylene balance tray and immediately dried with hot air using a dryer. After repeating these operations several times, the resulting balance tray was placed in a 50° C. oven and dried overnight and a film was then exfoliated from the balance tray to measure its water vapor permeability.

Example 2

To a coating pan (DRC-200; Powrex Corporation), 20 g of a montelukast sodium tablet (Singulair (registered trademark) tablet, 10 mg; Banyu Pharmaceutical Co., Ltd.) and 230 g of a placebo tablet (for bulking) were loaded, and the montelukast sodium tablet was coated with the coating agent of Example 1 to a film thickness of 60 to 80 µm. The resulting coated montelukast sodium tablet was stored for one week at a temperature of 40° C. and a relative humidity of 75% to examine the dissolution profile and the increase in moisture absorption before and after the storage.

Example 3

To 111.95 parts by mass of water, 5.25 parts by mass of a PEG (Macrogol 6000; NOF Corporation) and 382.8 parts by mass of 3.2% BT solution were added, and the resultant was stirred using a homogenizer to obtain a coating agent (hereinafter, referred to as "the coating agent of Example 3"). As the 3.2% BT solution, a filtrate which was obtained by adding 32 parts by mass of BT (Kunipia-F; Kunimine Industries Co., Ltd.) to 968 parts by mass of stirred water, uniformly dispersing the resulting solution using a homogenizer, and then centrifuging the resultant and suction-filtering the thus obtained supernatant through a filter paper was employed.

Thereafter, the coating agent of Example 3 was sprayed onto the back side of a polypropylene balance tray and immediately dried with hot air using a dryer. After repeating these operations several times, the resulting balance tray was placed in a 50° C. oven and dried overnight and a film was then exfoliated from the balance tray to measure its water vapor permeability. Also, the haze value of the coating agent of Example 3 was measured.

Example 4

Using a coating agent obtained by adding 5.25 parts by mass of a PEG (Macrogol 6000; NOF Corporation) and 272.2 parts by mass of 4.5% BT solution to 222.55 parts by mass of water and stirring the resultant using a homogenizer (hereinafter referred to as "the coating agent of Example 4"), a film was formed in the same manner as in Example 1 and its water vapor permeability and oxygen permeability coefficient were measured. Also, the haze value of the coating agent of Example 4 was measured.

Example 5

Using a coating agent obtained by adding 5.25 parts by mass of a PEG (Macrogol 1000 (average molecular weight 950 to 1,050); NOF Corporation) and 272.2 parts by mass of 4.5% BT solution to 222.55 parts by mass of water and stirring the resultant using a homogenizer, a film was formed in the same manner as in Example 1 and its water vapor permeability was measured.

Example 6

Using a coating agent obtained by adding 5.25 parts by mass of a PEG (Macrogol 4000 (average molecular weight: 2,600 to 3,800); NOF Corporation) and 272.2 parts by mass of 4.5% BT solution to 222.55 parts by mass of water and stirring the resultant using a homogenizer, a film was formed in the same manner as in Example 1 and its water vapor permeability was measured.

Example 7

Using a coating agent obtained by adding 5.25 parts by mass of a PEG (Macrogol 20000 (average molecular weight: 20,000 to 25,000); NOF Corporation) and 272.2 parts by mass of 4.5% BT solution to 222.55 parts by mass of water and stirring the resultant using a homogenizer, a film was formed in the same manner as in Example 1 and its water vapor permeability was measured.

Example 8

Using a coating agent obtained by adding 10.5 parts by mass of a PEG (Macrogol 6000; NOF Corporation) and 155.56 parts by mass of 4.5% BT solution to 333.94 parts by mass of water and stirring the resultant using a homogenizer, a film was formed in the same manner as in Example 1 and its water vapor permeability was measured.

Example 9

Using a coating agent obtained by adding 3.5 parts by mass of a PEG (Macrogol 6000; NOF Corporation) and 437.5 parts by mass of 3.2% BT solution to 59.0 parts by mass of water and stirring the resultant using a homogenizer, a film was formed in the same manner as in Example 1 and its water vapor permeability was measured.

Example 10

Using a coating agent obtained by adding 4.62 parts by mass of a PEG (Macrogol 6000; NOF Corporation), 336.9 parts by mass of 3.2% BT solution and 2.1 parts by mass of Span80 to 156.38 parts by mass of water and stirring the resultant using a homogenizer, a film was formed in the same manner as in Example 1 and its water vapor permeability was measured.

Example 11

Using a coating agent obtained by adding 4.62 parts by mass of a PEG (Macrogol 6000; NOF Corporation), 336.9 parts by mass of 3.2% BT solution and 2.1 parts by mass of Tween80 (Polysorbate 80) to 156.38 parts by mass of water and stirring the resultant using a homogenizer, a film was formed in the same manner as in Example 1 and its water vapor permeability was measured.

Example 12

Using a coating agent obtained by adding 5.075 parts by mass of a PEG (Macrogol 6000; NOF Corporation), 382.8 parts by mass of 3.2% BT solution and 0.175 parts by mass of liquid paraffin to 112.0 parts by mass of water and stirring the resultant using a homogenizer, a film was formed in the same manner as in Example 1 and its water vapor permeability was measured.

Example 13

To 544.4 parts by mass of 4.5% BT solution, 10.5 parts by mass of a PEG (Macrogol 6000; NOF Corporation) was added, and the resultant was stirred using a homogenizer. After adding thereto 3.5 parts by mass of Span20 and 531.15 parts by mass of water, 450.45 parts by mass of ethanol was further added and the resultant was stirred again using a homogenizer to obtain a coating agent (hereinafter, referred to as "the coating agent of Example 13").

Thereafter, 20 g of a montelukast sodium tablet (Singulair (registered trademark) tablet, 10 mg; Banyu Pharmaceutical Co., Ltd.) and 230 g of a placebo tablet (for bulking) were loaded to a coating pan (DRC-200; Powrex Corporation) and the montelukast sodium tablet was coated with the coating agent of Example 13 to a film thickness of 60 to 80 μm. The resulting coated montelukast sodium tablet was stored for one week at a temperature of 40° C. and a relative humidity of 75% to examine the increase in moisture absorption before and after the storage.

Further, the coating agent of Example 13 was sprayed onto the back side of a polypropylene balance tray and immediately dried with hot air using a dryer. After repeating these operations several times, the resulting balance tray was placed in a 50° C. oven and dried overnight and a film was then exfoliated from the balance tray to measure its water vapor permeability.

Example 14

To 127.4 parts by mass of 4.5% BT solution, 2.46 parts by mass of a PEG (Macrogol 6000; NOF Corporation) was added, and the resultant was stirred. After adding thereto 0.81 parts by mass of Span20 and 98.84 parts by mass of water, 225.55 parts by mass of ethanol was continuously added and the resultant was stirred using a homogenizer to obtain a coating agent. Using the thus obtained coating agent, a film was formed in the same manner as in Example 1 and its water vapor permeability was measured.

Example 15

To 76.23 parts by mass of 4.5% BT solution, 1.47 parts by mass of a PEG (Macrogol 6000; NOF Corporation) was added, and the resultant was stirred. After further adding thereto 2.10 parts by mass of Span20 and 120.2 parts by mass of water, the resultant was stirred using a homogenizer to obtain a coating agent. Using the thus obtained coating agent, a film was formed in the same manner as in Example 1 and its water vapor permeability was measured.

Example 16

To a high-speed stirring apparatus (FILMIX Model 40-40; PRIMIX Corporation) (hereinafter, referred to as "FIL-MIX"), 1.12 parts by mass of BT, 0.47 parts by mass of PEG 6000, 0.16 parts by mass of Span20 and 28.2 parts by mass of water were loaded and mixed with stirring for 5 minutes. Then, 20.0 parts by mass of water was continuously added thereto and the resultant was stirred using a stirrer and suction-filtered through a filter paper to obtain a coating agent.

Using the thus obtained coating agent, a film was formed in the same manner as in Example 1 and its water vapor permeability was measured.

Example 17

Using FILMIX, 22.4 parts by mass of 5.0% BT solution and 0.47 parts by mass of PEG 6000 were mixed with stirring for 5 minutes, and 0.16 parts by mass of Span20 was added thereto and mixed with stirring for another 5 minutes. Then, 26.97 parts by mass of water was added and the resultant was stirred using a stirrer and suction-filtered through a filter paper to obtain a coating agent. Using the thus obtained coating agent, a film was formed in the same manner as in Example 1 and its water vapor permeability was measured. As the 5.0% BT solution, a solution which was obtained by stirring 1.25 parts by mass of BT and 23.75 parts by mass of water using FILMIX was employed.

(Production of Olmesartan Medoxomil Core Tablet for Coating)

Since a commercially available tablet is a flat uncoated tablet and is thus not suitable for film coating, the tablet was pulverized and re-tableted into an R tablet. A commercially available olmesartan medoxomil-containing tablet (Olmetec tablet (registered trademark), 20 mg; Daiichi Sankyo Co., Ltd.) was pulverized using a mortar and the thus obtained pulverization product was re-tableted using a rotary tableting machine to obtain an olmesartan medoxomil core tablet (7 mm in diameter, 10R).

Example 18

The olmesartan medoxomil core tablet obtained by the above-described production method was loaded to a coating pan (DRC-200; Powrex Corporation) and coated with the coating agent of Example 1 to a film thickness of 60 to 80 μm. The thus obtained coated olmesartan medoxomil tablet and a commercially available metformin hydrochloride-containing tablet (Glycoran (registered trademark) tablet, 250 mg; Nippon Shinyaku Co., Ltd.) were placed in the same glass bottle. The glass bottle was capped with a plastic cap and stored for one week at a temperature of 40° C. and a relative humidity of 75%. The change in color of the metformin hydrochloride-containing tablet during the storage caused by diacetyl degraded and released from olmesartan medoxomil was evaluated using a color difference meter.

Comparative Example 1

Using a coating agent obtained by adding 12.25 parts by mass of a PEG (Macrogol 6000; NOF Corporation) and 164.1 parts by mass of 3.2% BT solution to 323.65 parts by mass of water and stirring the resultant using a homogenizer, a film was formed in the same manner as in Example 1 and its water vapor permeability was measured.

Comparative Example 2

Using a coating agent obtained by adding 1.75 parts by mass of a PEG (Macrogol 6000; NOF Corporation) and 492.2 parts by mass of 3.2% BT solution to 6.05 parts by mass of water and stirring the resultant using a homogenizer, a film was formed in the same manner as in Example 1 and its water vapor permeability was measured.

Comparative Example 3

Using a coating agent obtained by adding 5.25 parts by mass of a polyethylene oxide (PolyOX80, Dow Corning; hereinafter, referred to as "PEO") and 382.8 parts by mass of 3.2% BT solution to 111.95 parts by mass of water and stirring the resultant using a homogenizer, a film was formed in the same manner as in Example 1 and its water vapor permeability was measured.

Comparative Example 4

The gas-barrier coating agent according to Example 2 of WO '223 was prepared. To 156.38 parts by mass of water, 4.62 parts by mass of polyvinyl alcohol (Gohsenol EG-05, The Nippon Synthetic Chemical Industry Co., Ltd.; hereinafter, referred to as "PVA"), 336.9 parts by mass of 3.2% BT solution and 2.1 parts by mass of Span20 (sorbitan monolaurate) were added, and the resultant was stirred using a homogenizer to obtain a coating agent (hereinafter, referred to as "the coating agent of Comparative Example 4").

To a coating pan (DRC-200; Powrex Corporation), 25 g of a sodium valproate tablet (Depakene (registered trademark) tablet, 200 mg; Kyowa Hakko Kirin Co., Ltd.) and 225 g of a placebo tablet (for bulking) were loaded, and the sodium valproate tablet was coated with the coating agent of Comparative Example 4 to a film thickness of 50 to 60 μm. The resulting coated sodium valproate tablet was stored for 12 days at a temperature of 40° C. and a relative humidity of 75% to examine the change in the outer appearance and the dissolution profile before and after the storage. Further, a film was formed in the same manner as in Example 1 and its water vapor permeability was measured.

Comparative Example 5

To a coating pan (DRC-200; Powrex Corporation), 20 g of a montelukast sodium tablet (Singulair (registered trademark) tablet, 10 mg; Banyu Pharmaceutical Co., Ltd.) and 230 g of a placebo tablet (for bulking) were loaded, and the montelukast sodium tablet was coated with the coating agent of Comparative Example 4 to a film thickness of 50 to 60 μm. The resulting coated montelukast sodium tablet was stored for one week at a temperature of 40° C. and a relative humidity of 75% to examine the dissolution profile before and after the storage.

Comparative Example 6

Using a coating agent obtained by adding 1.37 parts by mass of polyethylene glycol 400 (PEG 400; NOF Corporation) and 100.0 parts by mass of 3.2% BT solution to 33.81 parts by mass of water and stirring the resultant using a homogenizer, a film was formed in the same manner as in Example 1 and its water vapor permeability was measured.

Comparative Example 7

To 65.34 parts by mass of 4.5% BT solution, 1.26 parts by mass of a PEG (Macrogol 6000; NOF Corporation) was added, and the resultant was stirred. After adding thereto 2.80 parts by mass of Span20 and 130.6 parts by mass of water, the resulting mixture was stirred using a homogenizer to obtain a coating agent. Using the thus obtained coating agent, a film was formed in the same manner as in Example 1 and its water vapor permeability was measured.

Comparative Example 8

The gas-barrier coating agent according to Example 2 of WO '765 was prepared. To 1,200 parts by mass of water, 15.0 parts by mass of dextrose (Japanese Pharmacopoeia dextrose, NG-TDA; San-ei Sucrochemical Co., Ltd.) and 35 parts by mass of sodium carboxymethylcellulose (T.P.T-JP 50; Gotoku Chemical Co., Ltd.) were added and dissolved with stirring to obtain a coating agent (hereinafter, referred to as "the coating agent of Comparative Example 8").

An olmesartan medoxomil core tablet (7 mm in diameter, 10R) was loaded to a coating pan (DRC-200; Powrex Corporation) and coated with the coating agent of Comparative Example 8 to a film thickness of 60 to 80 µm. The thus obtained coated olmesartan medoxomil tablet and a commercially available metformin hydrochloride-containing tablet (Glycoran (registered trademark) tablet, 250 mg; Nippon Shinyaku Co., Ltd.) were placed in the same glass bottle. The glass bottle was capped with a plastic cap and stored for one week at a temperature of 40° C. and a relative humidity of 75%. The change in color of the metformin hydrochloride-containing tablet during the storage caused by diacetyl degraded and released from olmesartan medoxomil was evaluated using a color difference meter.

Reference Example 1

A commercially available sodium valproate tablet (Depakene (registered trademark) tablet, 200 mg; Kyowa Hakko Kirin Co., Ltd.) was stored for 12 days at a temperature of 40° C. and a relative humidity of 75% and the outer appearance thereof was observed thereafter. Also, the dissolution profile was examined before and after the storage.

Reference Example 2

For a commercially available montelukast sodium tablet (Singulair (registered trademark) tablet, 10 mg; Banyu Pharmaceutical Co., Ltd.), the dissolution profile was examined before and after one week of storage at a temperature of 40° C. and a relative humidity of 75%.

Reference Example 3

For a commercially available montelukast sodium tablet (Singulair (registered trademark) tablet, 10 mg; Banyu Pharmaceutical Co., Ltd.), the increase in moisture absorption before and after one week of storage at a temperature of 40° C. and a relative humidity of 75% was calculated.

Reference Example 4

A commercially available olmesartan medoxomil-containing tablet (Olmetec tablet (registered trademark), 20 mg; Daiichi Sankyo Co., Ltd.) and a commercially available metformin hydrochloride-containing tablet (Glycoran (registered trademark) tablet, 250 mg; Nippon Shinyaku Co., Ltd.) were placed in the same glass bottle. The glass bottle was capped with a plastic cap and stored for one week at a temperature of 40° C. and a relative humidity of 75%. The change in color of the metformin hydrochloride-containing tablet during the storage caused by diacetyl degraded and released from olmesartan medoxomil was evaluated using a color difference meter.

Table 1 shows the haze values of the coating agent of Example 3 and the coating agent of Example 4.

TABLE 1

| | Haze value (%) |
|---|---|
| Example 3 | 85.44 |
| Example 4 | 37.68 |

Table 2 shows: the mass ratios of PEG, BT and the third component that were contained in the respective coating agents prepared in Examples 1 and 3 to 12 and Comparative Examples 1 to 4; the concentration of the respective BT solutions used in preparation of the coating agents; and the water vapor permeabilities of the respective films that were measured in Examples 1 and 3 to 12 and Comparative Examples 1 to 4.

TABLE 2

| | Mass percent of PEG in solid content of the coating agent | Mass percent of BT in solid content of the coating agent | Mass percent of third component in solid content of the coating agent | Concentration of BT dispersion solution used [%] | Water vapor permeability [g · mm/cm$^2$ 24 hr · atm] |
|---|---|---|---|---|---|
| Example 1 | 27.3 (7,300-9,300) | 63.7 | 9 (Span20) | 4.5 | $1.3 \times 10^{-5}$ |
| Example 3 | 30 (7,300-9,300) | 70 | — | 3.2 | $3.8 \times 10^{-5}$ |
| Example 4 | 30 (7,300-9,300) | 70 | — | 4.5 | $2.6 \times 10^{-5}$ |
| Example 5 | 30 (950-1,050) | 70 | — | 4.5 | $9.7 \times 10^{-5}$ |
| Example 6 | 30 (2,600-3,800) | 70 | — | 4.5 | $6.4 \times 10^{-5}$ |
| Example 7 | 30 (20,000-25,000) | 70 | — | 4.5 | $6.3 \times 10^{-5}$ |
| Example 8 | 60 (7,300-9,300) | 40 | — | 4.5 | $9.7 \times 10^{-5}$ |
| Example 9 | 20 (7,300-9,300) | 80 | — | 3.2 | $9.4 \times 10^{-5}$ |
| Example 10 | 26.4 (7,300-9,300) | 61.6 | 12 (Span80) | 3.2 | $5.2 \times 10^{-5}$ |
| Example 11 | 26.4 (7,300-9,300) | 61.6 | 12 (Tween80) | 3.2 | $5.8 \times 10^{-5}$ |
| Example 12 | 29 (7,300-9,300) | 70 | 1 (liquid paraffin) | 3.2 | $3.8 \times 10^{-5}$ |
| Comparative Example 1 | 70 (7,300-9,300) | 30 | — | 3.2 | $1.7 \times 10^{-4}$ |

TABLE 2-continued

|  | Mass percent of PEG in solid content of the coating agent | Mass percent of BT in solid content of the coating agent | Mass percent of third component in solid content of the coating agent | Concentration of BT dispersion solution used [%] | Water vapor permeability [g·mm/cm² 24 hr·atm] |
|---|---|---|---|---|---|
| Comparative Example 2 | 10 (7,300-9,300) | 90 | — | 3.2 | $2.8 \times 10^{-4}$ |
| Comparative Example 3 | — | 70 | 30 (PEO) | 3.2 | $7.5 \times 10^{-4}$ |
| Comparative Example 4 | — | 61.6 | 26.4 (PVA) 12 (Span20) | 3.2 | $1.9 \times 10^{-5}$ |

From these results, it was revealed that the water vapor permeability is less than $1.0 \times 10^{-4}$ g·mm/cm²·24 hr·atm when the mass ratio of the PEG and the swelling clay is in the range of 2:8 to 6:4, and those films formed by the coating agents of the respective Examples were proven to have excellent gas barrier properties that are equivalent to those of a PTP sheet. This means that, by forming a thin film layer on the surface of a pharmaceutical solid preparation with the coating agent for our pharmaceutical solid preparation to coat the pharmaceutical solid preparation, excellent gas barrier properties that are equivalent to those of a PTP sheet can be imparted to the pharmaceutical solid preparation itself.

The film formed in Example 4 had an oxygen permeability coefficient of $1.4 \times 10^{-5}$ cm³·mm/cm²·24 hr·atm, which was less than $1.0 \times 10^{-4}$ cm³·mm/cm²·24 hr·atm. From this result, it was revealed that a film formed by the coating agent for our pharmaceutical solid preparation has excellent gas barrier properties that are equivalent to those of a PTP sheet not only for water vapor, but also for oxygen.

Table 3 shows the observation results of the outer appearances of the tablet of Example 1, the tablet of Comparative Example 4 and a commercially available sodium valproate tablet.

TABLE 3

|  | Observation of Outer Appearance | |
|---|---|---|
|  | After 1 day | After 12 days |
| Tablet of Example 1 | Same as before storage | Same as before storage |
| Tablet of Comparative Example 4 | Same as before storage | Same as before storage |
| Commercially available tablet | Changed after storage | — |

According to the results, while a change in the outer appearance (deliquescence) was observed for the commercially available sodium valproate tablet after one day of storage, no change in the outer appearance was observed for those sodium valproate tablets whose surface was coated with a thin film layer formed by the coating agent for our pharmaceutical solid preparation (the tablets of Example 1 and Comparative Example 4) even after 12 days of storage. From these results, it was revealed that, by coating a pharmaceutical solid preparation with the coating agent for our pharmaceutical solid preparation such that a thin film layer is formed on the surface, the pharmaceutical solid preparation is imparted with gas barrier properties that are equivalent to those of a solid preparation coated with the gas barrier coating agent of WO '223.

Figure 1:
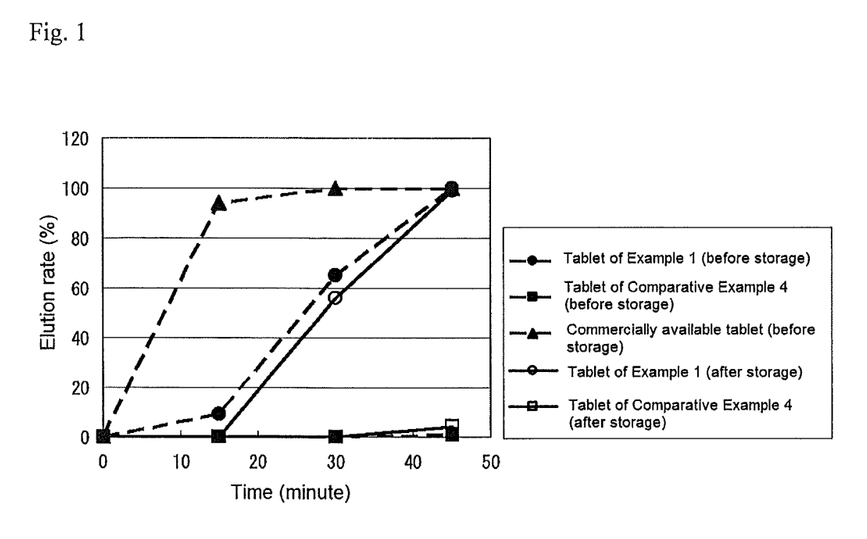
FIG. 1 shows the dissolution profiles of the tablets of Example 1 and Comparative Example 4 and a commercially available tablet.

Next, the effect of a gas barrier film coating on the dissolution profile was investigated. FIG. 1 shows the dissolution profiles of the tablets of Example 1 and Comparative Example 4 and a commercially available sodium valproate tablet.

According to the results shown in FIG. 1, while hardly any drug eluted from the tablet of Comparative Example 4 even after 45 minutes, the tablet of Example 1 and the commercially available sodium valproate tablet both showed almost 100% dissolution. From these results, it was revealed that there is absolutely no adverse effect on the disintegration properties of a pharmaceutical solid preparation itself even when it is coated with a film layer formed on the surface using the coating agent for our pharmaceutical solid preparation. It is noted here that, for the commercially available sodium valproate tablet after the storage, the dissolution test could not be performed since sodium valproate deliquesced during the storage.

From the above-described results, as a pharmaceutical preparation, our tablet was proven to be superior to the tablet according to WO '223 since, although the tablet according to WO '223 represented by Comparative Example 4 exhibited gas barrier properties, it was observed with a markedly delayed dissolution as compared to our tablet shown in Example 1.

FIG. 2s (FIGS. 2-1, 2-2, 2-3 and 2-4) show the dissolution profiles of the tablets of Example 2 and Comparative Example 5 and a commercially available montelukast sodium tablet.

Figure 22:
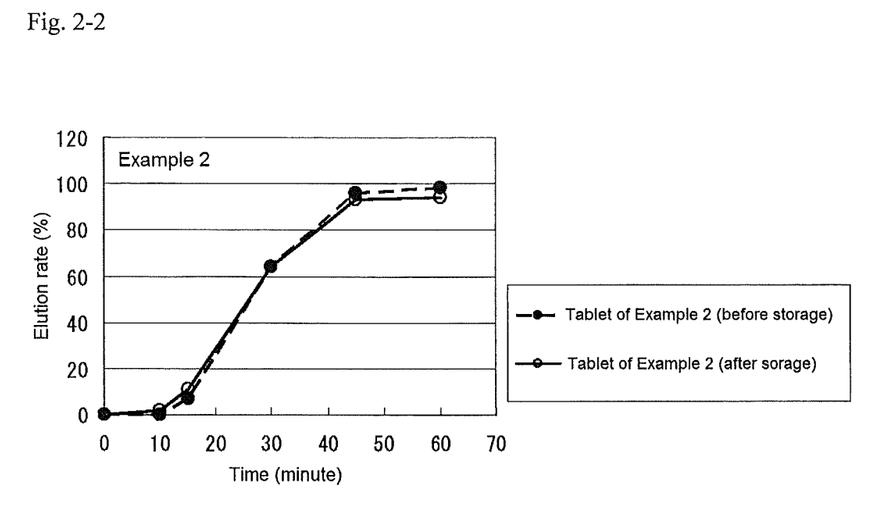
Figure 23:
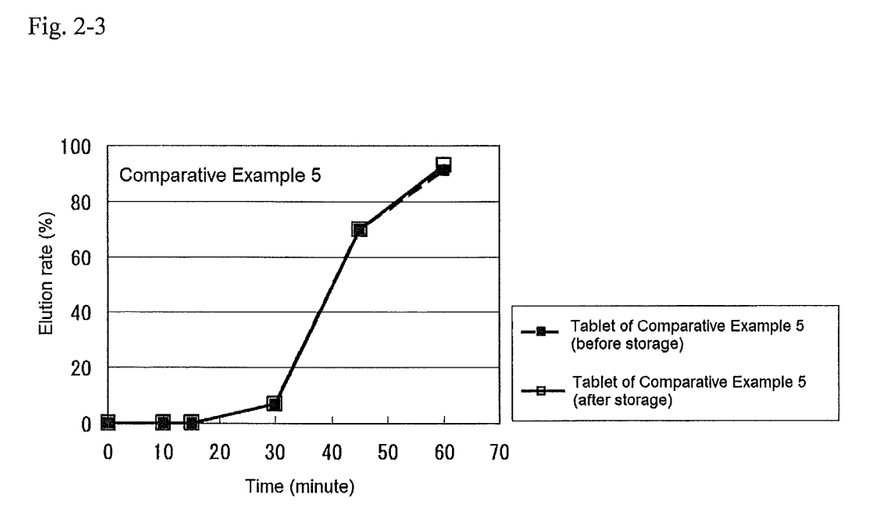
Figure 24:
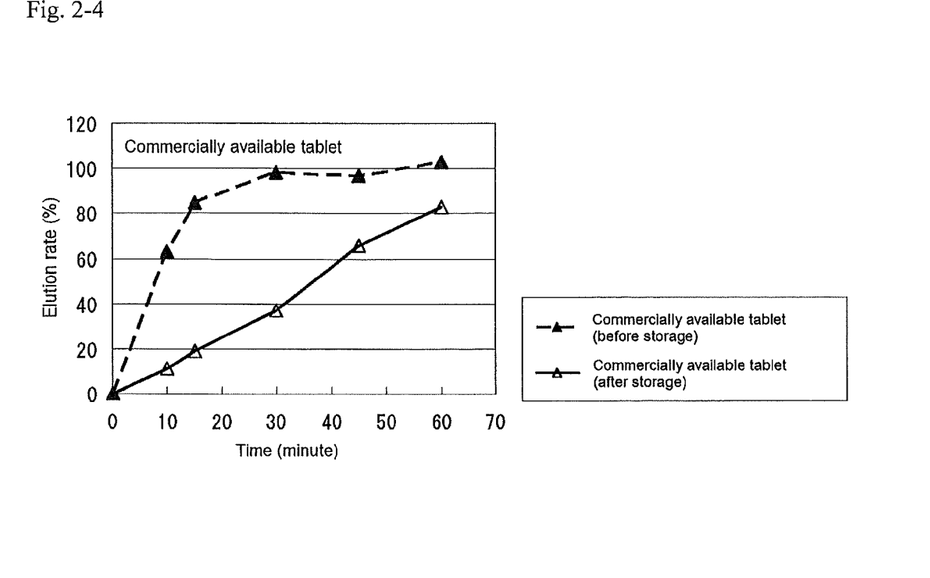

From the results shown in FIG. 2s, the commercially available montelukast sodium tablet was confirmed to absorb moisture during storage and exhibit a markedly delayed dissolution profile (FIG. 2-4). Meanwhile, there was no delay in dissolution caused by storage was observed for the tablets of Example 2 and Comparative Example 5 (FIGS. 2-2 and 2-3). Furthermore, while dissolution of drug from the tablet of Example 2 began about 15 minutes after the start of the test, in the tablet of Comparative Example 5, dissolution began about 30 minutes after the start of the test (FIGS. 2-2 and 2-3). These results mean that those pharmaceutical solid preparations whose surface was coated with a film layer formed by the coating agent for our pharmaceutical solid preparation retained the property of rapid drug dissolution because the film itself had disintegration properties.

From the above-described results, as a pharmaceutical preparation, our tablet was proven to be superior to the tablet according to WO '223 since, although the tablet according to WO '223 represented by Comparative Example 5 exhibited gas barrier properties, it was observed with a markedly delayed dissolution as compared to our tablet shown in Example 2.

(TEM Measurement of Film)

Figure 3:
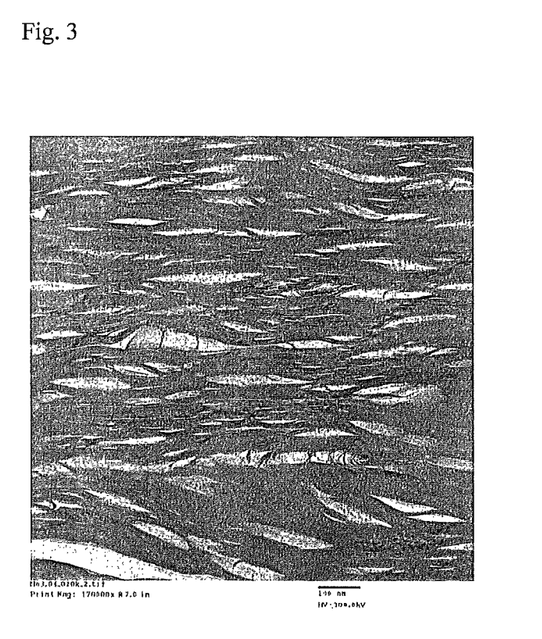
FIG. 3 is an image showing the film of Example 3, which was taken under a focused ion beam transmission electron microscope.

Using a focused ion beam method, the cross-sections in the thickness direction of the respective films formed in Examples 3 and 4 were observed under a TEM. FIG. 3 shows a micrograph of the film formed in Example 3 and FIG. 4 shows a micrograph of the film formed in Example 4.

Figure 4:
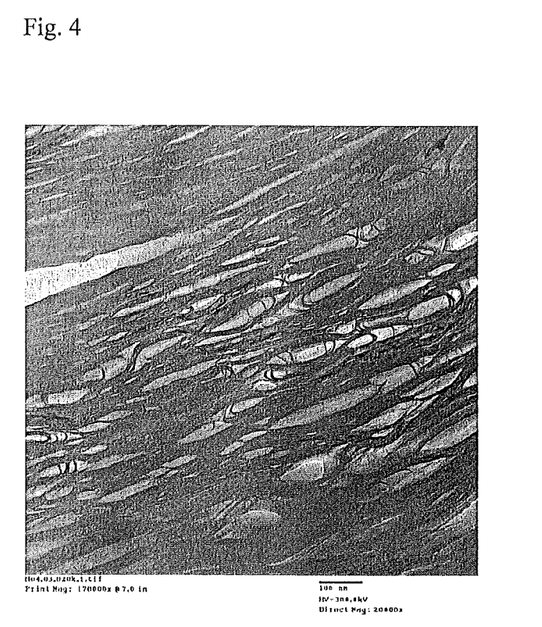
FIG. 4 is an image showing the film of Example 4, which was taken under a focused ion beam transmission electron microscope.
Figure 21:
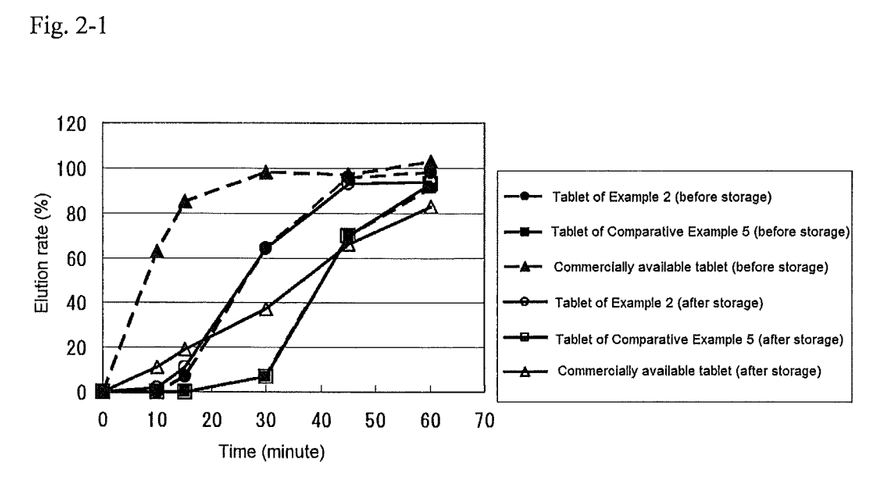

From the results shown in FIGS. 3 and 4, it was revealed that, in these films formed by the coating agent for our pharmaceutical solid preparation, the swelling clay was uniformly dispersed in the form of a belt-like laminated structure.

Table 4 shows the water vapor permeabilities of the films of Examples 13 and 14 where ethanol was used as a dissolution solvent of the coating agent. Table 5 shows the increase in moisture absorption by the coated montelukast sodium-containing tablets of Examples 2 and 13 after being stored at 40° C. and 75% RH.

where 30% ethanol was used as a dissolution solvent exhibited remarkable gas barrier properties with a water vapor permeability of $8.6 \times 10^{-6}$ g·mm/cm$^2$·24 hr·atm. Furthermore, according to the results shown in Table 5, while the commercially available tablet, a reference example, showed an increase in moisture absorption by 3.9%, the coated montelukast sodium-containing tablet of Example 2 where water was used as a coating solvent and the coated montelukast sodium-containing tablet of Example 13 showed an increase in moisture absorption by 2.5% and 1.6%, respectively.

TABLE 4

| | Mass percent of PEG in solid content of the coating agent | Mass percent of BT in solid content of the coating agent | Mass percent of third component in solid content of the coating agent | Solid content [%] | Dissolution solvent | Water vapor permeability [g · mm/cm$^2$ 24 hr · atm] |
|---|---|---|---|---|---|---|
| Example 1 | 27.3 (7,300-9,300) | 63.7 | 9 (Span20) | 3.5 | water | $1.3 \times 10^{-5}$ |
| Example 13 | 27.3 (7,300-9,300) | 63.7 | 9 (Span20) | 2.5 | 30% ethanol | $8.6 \times 10^{-6}$ |
| Example 14 | 27.3 (7,300-9,300) | 63.7 | 9 (Span20) | 2.0 | 50% ethanol | $2.7 \times 10^{-5}$ |

TABLE 5

| | Increase in Moisture Absorption (% by mass) |
|---|---|
| Reference Example 3 (commercially available tablet) | 3.9 |
| Example 2 | 2.5 |
| Example 13 | 1.6 |

According to the results shown in Table 4, the films of Examples 13 and 14 where ethanol was used as a dissolution solvent had a water vapor permeability of less than $1.0 \times 10^{-4}$ cm$^3$·mm/cm$^2$·24 hr·atm, so that it was revealed that excellent gas barrier properties equivalent to those of a PTP sheet could be imparted to the pharmaceutical solid preparations themselves in the same manner as in Example 1 where the dissolution solvent was water. In particular, the film of Example 13

Therefore, it was revealed that our coating agent imparts high gas barrier performance to a pharmaceutical solid preparation.

Table 6 shows the water vapor permeabilities of the film prepared with PEG 1000 (Example 5) and the film prepared with PEG 400 (Comparative Example 6).

TABLE 6

| | Mass percent of PEG in solid content of the coating agent | Mass percent of BT in solid content of the coating agent | Mass percent of third component in solid content of the coating agent | Concentration of BT dispersion solution used [%] | Water vapor permeability [g · mm/cm$^2$ 24 hr · atm] |
|---|---|---|---|---|---|
| Example 5 | 30 (950-1,050) | 70 | — | 4.5 | $9.7 \times 10^{-5}$ |
| Comparative Example 6 | 30 (380-420) | 70 | — | 3.2 | $1.5 \times 10^{-4}$ |

While the film of Comparative Example 6 where a PEG having a molecular weight distribution of 380 to 420 was used had a water vapor permeability of not less than $1.0 \times 10^{-4}$ cm$^3$·mm/cm$^2$·24 hr·atm, the film of Example 5 where a PEG having a molecular weight distribution of 950 to 1,050 was used had a water vapor permeability of less than $1.0 \times 10^{-4}$ cm$^3$·mm/cm$^2$·24 hr·atm. Therefore, it was suggested that, to allow a pharmaceutical solid preparation to retain gas barrier performance equivalent to that of a PTP packaging sheet, the PEG is required to have a molecular weight distribution of not less than 950.

Table 7 shows the water vapor permeabilities of the films having different mass percent of the third component in the respective coating agents.

TABLE 7

|  | Mass percent of PEG in solid content of the coating agent | Mass percent of BT in solid content of the coating agent | Mass percent of third component in solid content of the coating agent | Concentration of BT dispersion solution used [%] | Water vapor permeability [g · mm/cm² 24 hr · atm] |
|---|---|---|---|---|---|
| Example 15 | 21 (7,300-9,300) | 49 | 30 (Span20) | 4.5 | 6.9 × 10⁻⁵ |
| Comparative Example 7 | 18 (7,300-9,300) | 42 | 40 (Span20) | 4.5 | 5.1 × 10⁻⁴ |

While the film of Example 15 where the mass percent of the third component was 30 had a water vapor permeability of less than $1.0 \times 10^{-4}$ cm³·mm/cm²·24 h·atm, the film of Comparative Example 7 where the mass ratio percent of the third component was 40% had a water vapor permeability of not less than $1.0 \times 10^{-4}$ cm³·mm/cm²·24 hr·atm. Therefore, it was suggested that, to allow a pharmaceutical solid preparation to retain gas barrier performance equivalent to that of a PTP packaging sheet, the mass percent of the third component to be added to the coating agent is required to be not higher than 30%.

Table 8 shows the water vapor permeabilities of the films that were formed by a coating agent prepared using FILMIX.

TABLE 8

|  | Mass percent of PEG in solid content of the coating agent | Mass percent of BT in solid content of the coating agent | Mass percent of third component in solid content of the coating agent | Apparatus used in preparation | Water vapor permeability [g · mm/cm² 24 hr · atm] |
|---|---|---|---|---|---|
| Example 1 | 27.3 (7,300-9,300) | 63.7 | 9 (Span20) | POLYTRON | 1.3 × 10⁻⁵ |
| Example 16 | 26.9 (7,300-9,300) | 64.0 | 9.1 (Span20) | FILMIX | 2.7 × 10⁻⁵ |
| Example 17 | 27.3 (7,300-9,300) | 64.0 | 9.1 (Span20) | FILMIX | 2.5 × 10⁻⁵ |

The films of Examples 16 and 17 that were prepared using FILMIX both had a water vapor permeability of less than $1.0 \times 10^{-4}$ cm³·mm/cm²·24 hr·atm. Therefore, it was revealed that the stirring dispersion apparatus to be used in the preparation of the coating agent is not restricted to a homogenizer (Polytron; Kinematica AG) and that, as long as the apparatus is capable of dispersing the components in such a manner that the resulting coating agent can be suction-filtered through a filter paper, regardless of whether the components are added in the form of a liquid or a solid such as powder, a coating agent which allows a pharmaceutical solid preparation to retain gas barrier performance equivalent to that of a PTP packaging sheet can be prepared.

Table 9 shows the values of ΔE. The ΔE values were determined by placing a set of the coated olmesartan medoxomil tablet of Example 18 and a commercially available metformin hydrochloride-containing tablet, a set of the gas-barrier coating agent of Comparative Example 8 and a commercially available metformin hydrochloride-containing tablet or a set of the commercially available olmesartan medoxomil-containing tablet of Reference Example 4 and a commercially available metformin hydrochloride-containing tablet in the same bottle, storing the bottle for one week at 40° C. and 75% RH, and then evaluating the change in color of the respective metformin hydrochloride-containing tablets before and after the storage using a color difference meter.

TABLE 9

|  | ΔE |
|---|---|
| Example 18 | 0.6 |
| Comparative Example 8 | 16 |
| Reference Example 4 | 47 |

As a result, the metformin hydrochloride tablet which was stored in the same bottle as the coated olmesartan medoxomil tablet of Example 18 showed a ΔE value clearly smaller than that of the metformin hydrochloride tablet stored in the same bottle as the gas-barrier coating agent of Comparative Example 8. From this, it was revealed that an olmesartan medoxomil tablet coated with the coating agent for our pharmaceutical solid preparation inhibits color change of a metformin hydrochloride-containing tablet during storage caused by diacetyl degraded and released from olmesartan medoxomil. Furthermore, it was suggested that the gas barrier effects of the coating agent for our pharmaceutical solid preparation are superior as compared to the gas barrier technology disclosed in WO '765.

INDUSTRIAL APPLICABILITY

In the field of pharmaceuticals, the coating agent for a pharmaceutical solid preparation can be suitably used in the formation of a film layer for coating a pharmaceutical solid preparation.

The invention claimed is:

1. A coating agent comprising a polyethylene glycol having an average molecular weight of 950 to 25,000 and a swelling clay, wherein the mass percent of said polyethylene glycol and said swelling clay is 20:80 to 60:40, wherein the mass percent of the swelling clay in the film formed thereby is not less than 20, a sum of the polyethylene glycol and the swelling clay occupies not less than 70% mass percent of a film formed from the coating agent, the mass percent of the polyethylene glycol in a film formed by the coating agent is not less than 20%, the swelling clay is in a swollen state, and the agent does not comprise polyvinyl alcohol and wherein the coating agent, when coated on a solid preparation, disintegrates in a dissolution test at 37° C. using a paddle method at 50 rounds/min in 900 ml of water within 10 minutes in case of a size of 1 cm×2 cm and a thickness of 60 μm.

2. The coating agent according to claim 1, wherein said swelling clay is bentonite or aluminum magnesium silicate.

3. The coating agent according to claim 1, further comprising a sugar alcohol derivative surfactant in an amount of 0.5 to 30 mass percent of the solid content of the coating agent.

4. The coating agent according to claim 3, wherein said sugar alcohol derivative surfactant is a sorbitan fatty acid ester.

5. A pharmaceutical film formulation comprising the coating agent according to claim 1, having a water vapor permeability of less than $1.0 \times 10^{-4}$ g·mm/cm$^2$·24 h·atm at a room temperature of 40° C. and a relative humidity of 75%.

6. A coated pharmaceutical solid preparation coated with the coating agent according to claim 1, having a water vapor permeability of less than $1.0 \times 10^{-4}$ g·mm/cm$^2$·24 h·atm at a room temperature of 40° C. and a relative humidity of 75%.

7. The coating agent according to claim 2, further comprising a sugar alcohol derivative surfactant in an amount of 0.5 to 30 mass percent of the solid content of the coating agent.

8. The coating agent according to claim 7, wherein said sugar alcohol derivative surfactant is a sorbitan fatty acid ester.

9. A pharmaceutical film formulation comprising the coating agent according to claim 2, having a water vapor permeability of less than $1.0 \times 10^{-4}$ g·mm/cm$^2$·24 hr·atm at a room temperature of 40° C. and a relative humidity of 75%.

10. A pharmaceutical film formulation comprising the coating agent according to claim 3, having a water vapor permeability of less than $1.0 \times 10^{-4}$ g·mm/cm$^2$·24 h·atm at a room temperature of 40° C. and a relative humidity of 75%.

11. A pharmaceutical film formulation comprising the coating agent according to claim 4, having a water vapor permeability of less than $1.0 \times 10^{-4}$ g·mm/cm$^2$·24 hr·atm at a room temperature of 40° C. and a relative humidity of 75%.

12. A pharmaceutical film formulation comprising the coating agent according to claim 7, having a water vapor permeability of less than $1.0 \times 10^{-4}$ g·mm/cm$^2$·24 h·atm at a room temperature of 40° C. and a relative humidity of 75%.

13. A pharmaceutical film formulation comprising the coating agent according to claim 8, having a water vapor permeability of less than $1.0 \times 10^{-4}$ g·mm/cm$^2$·24 h·atm at a room temperature of 40° C. and a relative humidity of 75%.

14. A coated pharmaceutical solid preparation coated with the coating agent according to claim 2, having a water vapor permeability of less than $1.0 \times 10^{-4}$ g·mm/cm$^2$·24 h·atm at a room temperature of 40° C. and a relative humidity of 75%.

15. A coated pharmaceutical solid preparation coated with the coating agent according to claim 3, having a water vapor permeability of less than $1.0 \times 10^{-4}$ g·mm/cm$^2$·24 hr·atm at a room temperature of 40° C. and a relative humidity of 75%.

16. A coated pharmaceutical solid preparation coated with the coating agent according to claim 4, having a water vapor permeability of less than $1.0 \times 10^{-4}$ g·mm/cm$^2$·24 hr·atm at a room temperature of 40° C. and a relative humidity of 75%.

17. A coated pharmaceutical solid preparation coated with the coating agent according to claim 7, having a water vapor permeability of less than $1.0 \times 10^{-4}$ g·mm/cm$^2$·24 hr·atm at a room temperature of 40° C. and a relative humidity of 75%.

18. A coated pharmaceutical solid preparation coated with the coating agent according to claim 8, having a water vapor permeability of less than $1.0 \times 10^{-4}$ g·mm/cm$^2$·24 hr·atm at a room temperature of 40° C. and a relative humidity of 75%.

* * * * *